United States Patent [19]

Szalay

[11] 4,343,905
[45] Aug. 10, 1982

[54] CONCENTRATED GTF CHROMIUM COMPLEX BREWERS YEAST AND PROCESS FOR PRODUCING SAME

[76] Inventor: Andrew Szalay, 99 Buckingham Dr., Hackensack, N.J. 07601

[21] Appl. No.: 166,454

[22] Filed: Jul. 7, 1980

[51] Int. Cl.$^3$ .......................... C12N 1/16; C12N 1/18; A61K 35/78
[52] U.S. Cl. .................................... 435/256; 424/195; 435/255; 426/62
[58] Field of Search .................. 424/195; 426/62, 656; 435/256; 260/438.5 C

[56] References Cited

FOREIGN PATENT DOCUMENTS 724966  2/1955  United Kingdom ................ 426/62

OTHER PUBLICATIONS

J. Agr. Food Chem., vol. 21, No. 1, (1973), pp. 69–73.

Primary Examiner—Donald B. Moyer
Attorney, Agent, or Firm—Bauer & Amer

[57] ABSTRACT

A method of concentrating the organic chromium complex in Brewer's yeast is taught comprising the steps of forming a nutritional media consisting of chromium oxide and quantities of amino acids selected from the group consisting of nicotinic acid, glycine, L-glutamic acid and L-cystein. The nutritional media is then admixed with a Brewer's yeast solution and permitted to react. Upon drying and concentrating it has been found that the resultant yeast powder has a chromium complex of at least about 2,000 mcg/mg over 80% of which is GTF active organic chromium complex.

7 Claims, No Drawings

CONCENTRATED GTF CHROMIUM COMPLEX BREWERS YEAST AND PROCESS FOR PRODUCING SAME

BACKGROUND OF THE INVENTION

The present invention relates generally to a Brewer's yeast composition and most particularly to a Brewer's yeast composition which has been specially processed to synthetically concentrate the GTF (glucose tolerance factor) chromium complex naturally occurring in the yeast.

It has recently been discovered that the presence of chromium as an inorganic salt in food results in an increase in glucose oxidation in a human's biological system, particularly when extracts of Brewer's yeast containing chromium are added While not completely understood, it has been found that if an active GTF material is orally fed to an individual with diabetes, the GTF material will influence the pituitary gland to produce normal amounts of insulin. The relationship of chromium content in food and its effects on glucose oxidation activity are discussed, for example, in Toepfer et al, "Chromium Foods in Relation to Biological Activity" J. Agr. Food Chem. 21, 69 1973). Specifically, this article described the biological activity of various chromium containing foods and the relationship of GTF activity (expressed as a function of increased insulin response with the chromium) to the chromium content.

While Brewer's yeast has been found to naturally contain organic complexes of chromium believed to be GTF active, such complexes are naturally found in such minute quantities to limit, as a practical matter, the effect of such food. For example, in natural concentrations, one must consume almost one-half pound of Brewer's yeast to achieve any GTF activity. The Toepfer article indicates the calculated chromium biological value of Brewer's yeast is less than 45%. While many attempts have been made to concentrate the chromium-content of Brewer's yeast to a commercially viable amount, no one has heretofore been able to achieve a greater concentration, either naturally or synthetically.

Against the foregoing background, it is an object of the present invention to synthetically process Brewer's yeast to produce a more concentrated GTF chromium complex.

It is another object of the present invention to produce a yeast product having an active GTF chromium complex representing over 80% of the chromium present.

It is still another object of the present invention to produce an available chromium complex level over 80% using an economical process.

SUMMARY OF THE INVENTION

To the establishment of the above objects and advantages, the present invention briefly comprises a method of concentrating, the naturally occurring organic GTF active chromium complex in Brewer's yeast by reacting a standard Brewer's yeast solution with a nutritional complex media consisting of chromium oxide and a group of amino acids selected from the group consisting of nicotinic acid, glycine, L-glutamic acid and L-cystein. After drying and concentration, the resultant Brewer's yeast product has been found to have a chromium complex in an amount greater than about 2,000 mcg/mg, over 80% of which is GTF active.

DESCRIPTION OF THE PREFERRED EMBODIMENT

The present invention contemplates a naturally occurring Brewer's yeast composition which has been processed in such a manner by reaction with chromium oxide and a number of different amino acids so as to concentrate the GTF chromium complexes inherent in the yeast in order to produce a commercial product having a high GTF activity level.

To this end, a standard Nutritional Liquid and complex media for live Brewer's yeast is prepared by charging an amount of water, preferably about 25 liters in a vessel. With constant agitation and at a temperature of between about 85° C. and about 95° C., the first introduction of an amino acid is made. This first introduction, between about 475 and 525 grams of nicotinic acid constitutes between about 29 and about 32% by weight percent of solids in the complex media. This introduction is then followed by a second amino acid introduction consisting of between about 275 and 325 grams of glycine and between about 275 and 325 grams of L-glutamic acid, or 17–20% of each by weight of solids in the media. In a particularly preferred embodiment, the first and second additions of amino acid are made at a temperature of about 90° C., and the first amino acid addition comprises about 490 grams or about 30% of nicotinic acid and the second, 294 grams or 18.5% by weight of glycine and L-glutamic acid. It has been found that amino acid additions in amounts outside of the aforementioned ranges will produce a yeast composition with reduced GTF activity.

Following these two amino acid additions, a solution of chromium oxide, diluted in a ratio of between about 190 and and about 215 grams of chromium oxide or between about 11% and about 14% expressed as a weight percent of solids in the media to 2.3 liters of water, is then added to this at a temperature of between about 85° C. and about 95° C. and under constant agitation. A particularly preferred amount of chromium oxide is 205 grams or about 29% of the solids portion of the media.

A third amino acid addition is then made consisting of between about 290 and about 320 grams or between about 18 and about 21% by weight of solids in the media and preferably about 306 grams or 19.3% of L-cystein hydrochloride. The nutritional liquid and complex media, consisting of the amino acid and chromium oxide solution, should then be maintained at between about 85° C. and about 95° C. under constant agitation for a sufficient period of time to permit complete mixture, generally about 60 minutes, after which it should be allowed to cool and stabilize. In many instances, stabilization may take 48 hours.

During stabilization of the amino acid and chromium oxide solution, a solution of Brewer's yeast is prepared by admixing between about 400 and about 550 Kg preferably between about 460 and about 500 Kg of standard Brewer's yeast solids per 1,000 gallons of water under agitation, aeration, and at a temperature conducive to permit growth of the yeast, preferably between about 20° and about 35° C. When prepared in different quantities, the ratio of media to yeast solids should be between about 0.3 and about 0.4% of media to yeast and preferably about 0.35%. The temperature of the yeast solution is then raised to between about 35° and about 40° whereupon the amino acid and chromium oxide solution are added with constant agitation. Agitation should be continued for a period of time and at a temperature sufficient to permit complete admixture and reaction between the yeast and the amino acids and chromium oxide solution, preferably a minimum of twenty-four hours at between about 35° and about 40° C.

After complete admixture and reaction between the amino acids, the chromium oxide solution and the yeast, the temperature of the resultant yeast slurry is then raised to a temperature sufficiently high to kill the yeast, preferably at least about 90° C., and for a period of time of generally at least about 3 hours. It is understood that, if desired, the yeast may be killed in other conventional means or at higher temperatures for shorter periods of time. The yeast slurry is then spray dried in a conventional manner and then assayed or, if preferred, processed further. Using standard assay techniques, the yeast produced will contain approximately 200 mcg/gm of GTF chromium complexes measured in terms of chromium content.

The chromium content of the yeast can be further increased in potency to at least about 2,000 mcg/gm by hydrolyzation wherein the spray dried yeast is introduced into a conventional hydrolyzation reactor to which water is added and a yeast prepared solution at temperatures slightly above ambient and with constant agitation. Proteolytic enzymes are then added in an amount sufficient to digest the yeast cells. The soluble are then separated from the insoluble yeast cells by use of conventional centrifugation or filtration. The soluble yeast portion containing the GTF chromium complexes is then spray dried and then is ready for final assay and standardization.

The resultant Brewer's yeast product, after hydrolyzation, exhibits the following characteristics and properties:

| Description | powder |
| --- | --- |
| Color | off white to grayish white |
| odor | slight |
| taste | yeast type |
| loss on drying | 6% maximum |

The chromium in the yeast product is in an organically bound trivalent configuration with the following amino acides typically found in Brewer's yeast: cystine, glutamic acid, glycine, isoleucine, leucine, methionine, phenylalanine, threonine, tryptophane and valine. The chromium content measured using a spectrophotometer was 2,000 mcg/gm. Using conventional atomic absorption techniques, between about 80 and about 85% of the chromium present in the yeast is GTF active organic chromium complex.

The microbiological assay of the resultant yeast product is as follows:

| E coli | negative |
| --- | --- |
| salmonella | negative |
| total plate count | maximum 5,000/gm |

The following examples serve to illustrate certain preferred embodiments of the method for producing the yeast product of the present invention and are not to be construed as limiting the scope of the present invention.

EXAMPLE 1

In order to illustrate the yeast composition of the present invention, a nutritional liquid and complex media for the live yeast was prepared by charging a mitable stainless steel vessel equipped with an automatic temperature-controlled heating element with 25 liters of water. With constant agitation and at a temperature of 90° C., 490 grams of nicotinic acid; 294 grams of glycine; and 294 grams of L-glutamic acid were added to the vessel followed by a chromium oxide solution consisting of 204 grams of chromium oxide dissolved in 2.3 liters of water. The chromium oxide solution was added in small incremental amounts while the temperature of the solution was maintained at 90° C.

Following the addition of the chromium oxide, 306 grams of L-cystine hydrochloride were added and agitation was continued for an additional 60 minutes at a temperature of 90° C. The solution was then permitted to settle undisturbed at ambient temperature and with no agitation for an additional 48 hours.

During settling of the nutritional liquid and complex media, a solution of Brewer's yeast was prepared in a stainless steel 1,000-gallon tank by introducing 460 Kg of Brewer's yeast solids and diluting it with 1,000 gallons of water. To permit the yeast to grow, the temperature was raised to 35° C. with constant agitation while bubbling air from the tank bottom. The settled liquid nutritional and complex media and yeast solutions were then admixed, agitated and maintained at a temperature of 35° C. for twenty-four hours at which time the temperature was raised to 90° C. and maintained for 3 hours to kill the yeast.

The yeast was then spray dried and hydrolyzed to concentrate the chromium complex by diluting the yeast with water and introducing a proteolytic enzyme to digest the yeast cells. The soluble yeast cells containing the active GTF chromium complexes were then separated from the insoluble by centrifugation, spray dried, and final assayed.

Final assay was conducted according to the following protocol. A 1,000 mg/l chromium standard was prepared by dissolving 511.5 mg of $CrCl_3.6H_2O$ in 100 ml of water from which was prepared, by dilution, a standard of 20 mg/l chromium in 50% ethanol/water. One gram of the dried yeast powder was added to 20 ml of 50% ethanol/water in a 50 ml beaker for 30 minutes. The solution was then filtered into a 25 ml flask and diluted with 50% ethanol/water. One ml of the resultant yeast solution was then added to each of four 10 ml flasks. The first flask labelled "B" was diluted with 50% ethanol/water. To the second flask, labeled "B+2ns/C," was added 1 ml of 20 ng/l standard; to the third flask, labeled "B+4 mg/l", was added 2 ml of 20 mg/l standard; and to the fourth flask, labeled "B+10 mg/l" was added 20 mg/l standard. Each flask was diluted to volume with 50% ethanol/water. An Instrumentation Laboratory IL453 atomic absorption spectrophotometer equipped with a chromium lamp and a deuterium lamp was used in the dual channel A-B mode. The chromium lamp was run at 7 mamps and the deuterium lamp at 20 mamps. The A and B monochromators were set at 357.9 nm, the A channel slit at 150 nm and the B channel slit at 450 nm. A nitrous oxide/acetylene burner head was used to produce the flame, the height setting of which was 9 mm. The pressure of the nitrous oxide was 25 lb./in$^2$ and the acetylene was 11 lb./in$^2$ at the cylinder. Flow rates were 11 ml/min. for the nitrous oxide and 4 ml/min for acetylene. A blank of 50% ethanol/water was used to zero the instrument. The B sample was read just followed by the standards and a plot of mg/l chromium added (X-axis) as absorbance (y-axis) was made. The X intercept at Y=0 was determined and the intercept multiplied by −1 will give the mg/l organic chromium in the 10 ml flask. The theoretical organic chromium concentration in the 10 ml flask was calculated using the concentration of total chromium in the yeast using the following formula:

$$\% \text{ organic chromium} = \frac{\text{Actual organic chromium concentration}}{\text{Total chromium concentration}} \times 100$$

When so measured, the % organic chromium in the resultant yeast powder was 80.8%.

EXAMPLE 2

In order to demonstrate the efficacy of the yeast compound of the present invention, a study was conducted wherein seventeen individual subjects consumed a daily supplement of the yeast product of Example 1 in an amount sufficient to contain 200 mcg/chromium per day for four months. Blood samples were taken prior to the commencement of the test and after completion at four months. The subjects were divided into 4 groups for statistical purposes, based on the initial blood test: normal (8 subjects); normal with abnormal glucose control (3 subjects); juvenile diabetics (5 subjects); mature diabetics (1 subject). The following results were obtained:

|  | "A" | "B" | "C" | "D" | Avg. |
|---|---|---|---|---|---|
| Cholesterol | | | | | |
| Before | 229mg/dl | 228mg/dl | 272mg/dl | 266mg/dl | 244mg/dl |
| After | 210mg/dl | 190mg/dl | 198mg/dl | 234mg/dl | 204mg/dl |
| % Change | 8%− | 17%− | 27%− | 12%− | 16%− |
| Triglycerides | | | | | |
| Before | 137mg/dl | 77mg/dl | 114mg/dl | 160mg/dl | 115mg/dl |
| After | 107mg/dl | 102mg/dl | 95mg/dl | 40mg/dl | 107mg/dl |
| % Change | 22%− | 32%+ | 17%− | 75%− | 7%− |
| HDL | | | | | |
| Before | 47mg/dl | 51mg/dl | 55mg/dl | 66mg/dl | 51mg/dl |
| After | 60mg/dl | 62mg/dl | 59mg/dl | 75mg/dl | 62mg/dl |
| % Change | 28%+ | 21%+ | 7%+ | 14%+ | 22%+ |
| Cholesterol/HDL | | | | | |
| Before | 4.9 | 4.6 | 4.9 | 4.0 | 4.8 |
| After | 3.9 | 3.0 | 3.5 | 3.1 | 3.6 |
| % Change | 20%− | 35%− | 29%− | 23%− | 25%− |
| Glycosylated Hemoglobin (GHB) | | | | | |
| Before | 8.3% | 17.4% | 11.6% | 13.7% | 11.1% |
| After | 6.4% | 7.2% | 7.0% | 7.3% | 6.8% |
| % Change | 23%− | 59%− | 34%− | 47%− | 38.7%− |

The cholesterol and tryglyceride levels generally decreased as a result of the chromium supplementation. HDL, which is a measurement of "good cholesterol," increased, which is beneficial. The HDL/cholesterol ratio, which is considered one of the best indicators of risk of heart disease, uniformly decreased substantially indicating a positive benefit from chromium supplementation. Glycosylated hemoglobin (GHb) represents blood glucose control and high GHb levels are apparent in diabetics All individuals treated exhibited improved glucose control (as a result of the chromium) and the GHb level of the diabetics became normal during the study.

Although the foregoing Examples illustrate the preparation of a particular type of yeast product and demonstrate the efficacy of that product, it will be appreciated that the teachings of the application encompass broader and other combinations than recited in the Examples.

Accordingly, the present invention should be limited only by the time scope of the appended claims.

What is claimed is:

1. A method for concentrating the naturally occurring GTF chromium complex in a Brewer's yeast compound by reacting a Brewer's yeast solution with a nutritional media solution including chromium oxide and amino acids selected from the group consisting of nicotinic acid, glycine, L-glutamic acid and L-cystein.

2. A method for concentrating the naturally occurring GTF chromium complex in a Brewer's yeast compound, said method comprising the steps of:
   preparing a nutritional and complex media including:
   between about 29% and about 32% by weight of solids of nicotinic acid;
   between about 17% and about 20% by weight of solids of glycine;
   between about 17% and about 20% by weight of solids of L-glutamic acid;
   between about 11% and about 14% by weight of solids of chromium oxide; and
   between about 18% and about 21% by weight of L-cystein;
   preparing a solution of Brewer's yeast wherein the yeast solids are diluted in water;
   admixing the media and yeast solution and permitting the admixed yeast solution to react with the media; and
   killing the yeast cells and spray drying the yeast solution to create a powder form.

3. The method of claim 2 wherein the GTF chromium complex of said spray dried yeast powder is further concentrated by subsequently hydrolyzing the dried powder.

4. The method of claim 2 wherein the Brewer's yeast solution is prepared at a ratio of between about 400 and about 500 Kg of yeast solids to 1,000 gallons of water.

5. The method of claim 4 wherein said media and said yeast solution are admixed in ratios of between about 0.3 and about 0.4% by weight of solids of the media to weight of solids of the yeast.

6. A method for producing a Brewer's yeast compound having a high concentration of GTF chromium complexes, said method comprising the steps of:

preparing a nutritional and complex media by diluting in water at a temperature of between about 85° C. and about 95° C.:
between about 29% and about 32% by weight of solids of nicotinic acid;
between about 17% and about 20% by weight of solids of glycine;
between about 17% and about 20% by weight of L-glutamic acid;
between about 11% and about 14% by weight of solids of chromium oxide diluted in water; and
between about 18% and about 21% by weight of L-cystein;
permitting the media to cool to ambient temperature;
preparing a Brewer's yeast solution of yeast solids diluted in water and maintaining said yeast solution at a temperature of between about 20° C. and about 35° C. to permit yeast growth;
raising the temperature of the yeast solution to at least 35° C., admixing the yeast solution and media and permitting the admixed solution to react;
killing the yeast cells by raising the temperature of the admixed solution to at least about 90° C.;
drying the yeast solution to form a powder; and
concentrating the chromium complex of said yeast.

7. The method of claim 6 wherein said chromium complex is concentrated by hydrolyzation.

* * * * *